(12) United States Patent
Gydesen et al.

(10) Patent No.: US 11,377,263 B2
(45) Date of Patent: Jul. 5, 2022

(54) DISPENSER WITH APPLICATOR TIP

(71) Applicant: 3M INNOVATIVE PROPERTIES COMPANY, St. Paul, MN (US)

(72) Inventors: Henry C. Gydesen, Oakdale, MN (US); Paul R. Klaiber, Mahtomedi, MN (US); Yizhong Wang, Woodbury, MN (US); Bruce R. Broyles, St. Paul, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 120 days.

(21) Appl. No.: 16/762,007

(22) PCT Filed: Nov. 1, 2018

(86) PCT No.: PCT/IB2018/058587
§ 371 (c)(1),
(2) Date: May 6, 2020

(87) PCT Pub. No.: WO2019/092562
PCT Pub. Date: May 16, 2019

(65) Prior Publication Data
US 2020/0307863 A1 Oct. 1, 2020

Related U.S. Application Data

(60) Provisional application No. 62/583,848, filed on Nov. 9, 2017.

(51) Int. Cl.
*A61J 1/06* (2006.01)
*B65D 25/42* (2006.01)
(Continued)

(52) U.S. Cl.
CPC .............. *B65D 25/42* (2013.01); *A61J 1/067* (2013.01); *A61J 1/1412* (2013.01);
(Continued)

(58) Field of Classification Search
CPC ...... B65D 35/38; B65D 1/095; B65D 1/0238; A46B 11/002; A46B 11/0003;
(Continued)

(56) References Cited

U.S. PATENT DOCUMENTS 2,930,063 A  3/1960 Stull
3,782,066 A  1/1974 Schmitt
(Continued)

FOREIGN PATENT DOCUMENTS

AU  1974988  1/1989
CA  2796699  5/2014
(Continued)

OTHER PUBLICATIONS

Data Sheet, Tubes Twist-off tabs & small screw caps, [online], Albea, Paris, France, Retrieved from the Internet], URL: <http://mixandmatch.albea-group.com>, 1 page.
(Continued)

*Primary Examiner* — Paul R Durand
*Assistant Examiner* — Randall A Gruby
(74) *Attorney, Agent, or Firm* — Ashley M. Dreis; 3M Innovative Properties Company

(57) ABSTRACT

A dispenser (1) for liquids includes a reservoir (100) defining a volume (V100) for housing a liquid (150); a delivery tube (200) with a first end (201) attached to the reservoir, and a second end (202) distal from the reservoir, the delivery tube including a passage (203) in fluid communication with the volume of the reservoir and extending away from the reservoir; an applicator element (300) including an applicator tip (320) and a base (310) attached to the second end of the delivery tube, the applicator tip having a plurality of fingers (322) extending away from the base to a distal end of the applicator element distal from the delivery tube; and a removable seal (340), wherein removal of the removable (Continued)

seal creates an opening in the passage at a location upstream of the applicator tip and a fluid distribution channel between the fingers.

18 Claims, 13 Drawing Sheets

(51) Int. Cl.
*A61J 1/14* (2006.01)
*A61M 35/00* (2006.01)
*B05C 17/005* (2006.01)
*B65D 1/09* (2006.01)

(52) U.S. Cl.
CPC ..... *A61M 35/003* (2013.01); *B05C 17/00516* (2013.01); *B05C 17/00583* (2013.01); *B65D 1/095* (2013.01); *B65D 2547/063* (2013.01)

(58) Field of Classification Search
CPC .. A46B 11/0041; A46B 11/0075; A61J 1/067; A61J 1/1412; A61M 35/003; B05C 17/00583
USPC ................. 222/206, 212–214; 215/250–254; 401/183–186, 286–290; 433/89
See application file for complete search history.

(56) References Cited

U.S. PATENT DOCUMENTS

| | | | |
|---|---|---|---|
| 3,847,151 A | 11/1974 | D'Alessandro | |
| 4,279,527 A | 7/1981 | Moe | |
| 4,648,532 A | 3/1987 | Green | |
| 4,688,703 A * | 8/1987 | Bayer | B65D 35/44 215/901 |
| 4,930,922 A | 6/1990 | LaRosa | |
| 4,990,016 A * | 2/1991 | Seidler | A45D 34/042 401/268 |
| 4,997,371 A | 3/1991 | Fischer | |
| 5,006,004 A | 4/1991 | Dirksing | |
| 5,066,157 A | 11/1991 | Lift | |
| 5,106,221 A | 4/1992 | Diot | |
| 5,119,803 A | 6/1992 | Fishman | |
| 5,186,563 A | 2/1993 | Gebhard | |
| 5,229,061 A | 7/1993 | Van Dyke | |
| 5,242,422 A | 9/1993 | Schneberger | |
| 5,246,371 A | 9/1993 | Fischer | |
| 5,509,906 A | 4/1996 | Poynter | |
| 5,791,801 A | 8/1998 | Miller | |
| 5,816,804 A | 10/1998 | Fischer | |
| 6,059,570 A * | 5/2000 | Dragan | A61C 5/50 433/80 |
| 6,299,012 B1 | 10/2001 | Redmond | |
| 6,328,715 B1 | 12/2001 | Dragan | |
| 6,382,972 B1 | 5/2002 | Fischer | |
| 6,422,866 B2 | 7/2002 | Dragan | |
| 6,547,467 B2 | 4/2003 | Quintero | |
| 6,585,511 B2 | 7/2003 | Dragan | |
| 6,595,969 B1 | 7/2003 | Emerit | |
| 6,626,308 B2 | 9/2003 | Weiler | |
| 6,652,176 B2 | 11/2003 | Dumler | |
| 6,846,459 B2 * | 1/2005 | Snedden | B29C 55/24 222/206 |
| 6,869,419 B2 | 3/2005 | Dragan | |
| 6,932,603 B2 | 8/2005 | Han | |
| 6,957,958 B2 | 10/2005 | Rowe | |
| 7,040,893 B2 * | 5/2006 | Fischer | A61C 5/62 433/80 |
| 7,243,789 B2 | 7/2007 | Discko, Jr. | |
| 7,431,529 B1 * | 10/2008 | Rushe | B65D 1/0238 401/133 |
| 7,435,027 B2 | 10/2008 | Hetzel | |
| 7,476,045 B2 | 1/2009 | Dumler | |
| 7,478,959 B2 | 1/2009 | Hohlbein | |
| 7,614,811 B2 | 11/2009 | Kaufman | |
| 7,740,479 B2 | 6/2010 | Allred | |
| 7,832,956 B2 | 11/2010 | Ross | |
| 7,934,512 B2 | 5/2011 | Spagnuolo | |
| 8,262,306 B2 | 9/2012 | Levine | |
| 8,267,609 B2 * | 9/2012 | Levine | A61M 35/003 433/89 |
| 8,292,529 B2 | 10/2012 | Francavilla | |
| 8,297,869 B2 | 10/2012 | Gueret | |
| 8,584,301 B2 | 11/2013 | Maissami | |
| 8,591,130 B2 | 11/2013 | Koptis | |
| 8,640,873 B2 | 2/2014 | Nakano | |
| 8,695,611 B2 | 4/2014 | Snedden | |
| 8,783,451 B2 | 7/2014 | Slokovic | |
| 8,851,779 B2 | 10/2014 | Jimenez | |
| 8,899,858 B2 | 12/2014 | Margoosian | |
| 9,016,968 B2 | 4/2015 | Thorpe | |
| 9,066,711 B2 | 6/2015 | Ruiz, Sr. | |
| 9,138,045 B2 * | 9/2015 | Habibi-Naini | A46B 11/0072 |
| 9,402,700 B2 | 8/2016 | Patel | |
| 9,578,949 B2 | 2/2017 | Villarreal | |
| 9,610,147 B2 | 4/2017 | Han | |
| 9,616,209 B2 | 4/2017 | Kaufman | |
| 10,179,678 B2 * | 1/2019 | Oliveira | B65D 47/106 |
| 10,201,408 B2 * | 2/2019 | Levine | A46B 11/00 |
| 2005/0045667 A1 | 3/2005 | Poynter | |
| 2005/0056970 A1 | 3/2005 | Foust | |
| 2006/0011666 A1 * | 1/2006 | Wurtz | B65D 1/095 222/541.1 |
| 2006/0247568 A1 | 11/2006 | Stenton | |
| 2007/0172789 A1 | 7/2007 | Muller | |
| 2007/0292366 A1 * | 12/2007 | Clarot | A61C 19/063 424/56 |
| 2010/0032432 A1 * | 2/2010 | Stull, Sr. | B65D 51/1616 220/257.1 |
| 2011/0082432 A1 | 4/2011 | Fontana | |
| 2011/0315720 A1 | 12/2011 | Marshall | |
| 2012/0051829 A1 | 3/2012 | Margoosian | |
| 2012/0189977 A1 | 7/2012 | Eke | |
| 2013/0104324 A1 | 5/2013 | Greer, Jr. | |
| 2014/0016981 A1 * | 1/2014 | Levine | A61C 19/066 401/28 |
| 2014/0212836 A1 | 7/2014 | Fritze | |
| 2015/0118646 A1 | 4/2015 | Peuker | |
| 2016/0045283 A1 | 2/2016 | Boehm | |
| 2016/0095414 A1 | 4/2016 | Debnath | |
| 2016/0206417 A1 | 7/2016 | Levine | |
| 2016/0262531 A1 | 9/2016 | Hellkamp | |
| 2017/0224099 A1 | 8/2017 | Lee | |
| 2020/0037743 A1 * | 2/2020 | Korup | A46B 11/0041 |

FOREIGN PATENT DOCUMENTS

| | | |
|---|---|---|
| CN | 2909940 | 6/2007 |
| DE | 2200310 | 7/1973 |
| EP | 0311721 | 4/1989 |
| EP | 0421984 | 4/1991 |
| EP | 1593351 | 11/2005 |
| EP | 2269558 | 1/2011 |
| FR | 2784285 | 4/2000 |
| WO | WO 1996-40445 | 12/1996 |
| WO | WO 2004-039209 | 5/2004 |
| WO | WO 2006-041465 | 4/2006 |
| WO | WO 2006-058139 | 6/2006 |
| WO | WO 2012-024788 | 1/2012 |
| WO | WO 2014-206988 | 12/2014 |
| WO | WO 2016-064594 | 4/2016 |

OTHER PUBLICATIONS

Product Information Sheet, Astroglide TTC®, [online], BioFilm IP LCC, Vista, California, 2017, Retrieved from the Internet], URL: <https://www.astroglide.com/ttc/about-ttc, 7 pages.
Product Information Sheet, MicroDose™ Blow-Fill-Seal Unit Dose Packaging, [online], Unicep, 2014, [retrieved on Nov. 14, 2017], Retrieved from the Internet], URL: https://www.unicep.com/packaging/microdose-blow-fill-seal-unit-dose>, 2 pages.

(56) References Cited

OTHER PUBLICATIONS

Product Information Sheet, Prochieve® Progesterone, [online], Columbia Laboratories, Inc., National Drug Codes List, [retrieved on Nov. 14, 2017], Retrieved from the Internet], URL: <https://ndclist.com/ndc/55056-0406>, 9 pages.

Product Information Sheet, Spadabravo Hair Dye Bottle Applicator, [online], XuanYuan Trade Co. Ltd., China [retrieved on Nov. 14, 2017], Retrieved from the Internet], URL: <https://www.aliexpress.com/item/Hair-Dye-Bottle-Applicator-120-ML-Brush-Dispensing-Bottles-Salon-Hair-Coloring-Dyeing-Styling-Tool/32829491397.html?spm=2114.search0104.3.1.1ghy7m&ws_ab_test=searchweb0_0,searchweb201602_1_10152_10065_10151_10344_10068_10130_10345_10324_10342_10547_10325_10343_10546_10340_10341_10548_10545_10541_10562_10084_10083_10307_5680011_10178_10060_10155_10154_10056_10055_10539_10312_10059_10313_10314_10534_10533_100031_10103_10073_10102_10557_10558_10142_ 10107-10102,searchweb201603_25,ppcSwitch_5&btsid=14f4ff73-ccc5-4aa1-95bd-9b63cf0b8a65&algo_expid=fe016747-c175-4585-a769-a90e54a25fd9-0&algo_expid=fe016747-c175-4585-a769-a90e54a25fd9>, 8 pages.

Varnish Pen Brochure, Young Dental, [online], Algonquin, Illinois [retrieved on on Nov. 14, 2017], Retrieved from the Internet], URL: <http://online.flipbuilder.com/exgo/lohu/mobile/index.html#p=1>, 12 pages.

International Search Report for PCT International Application No. PCT/IB2018/058587, dated Feb. 5, 2019, 6 pages.

\* cited by examiner

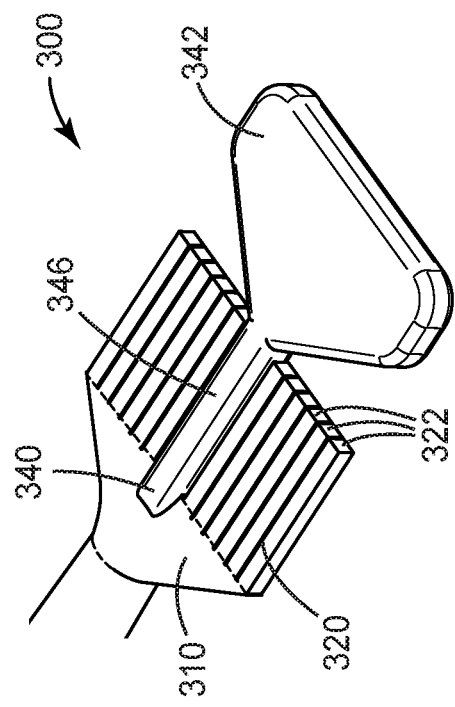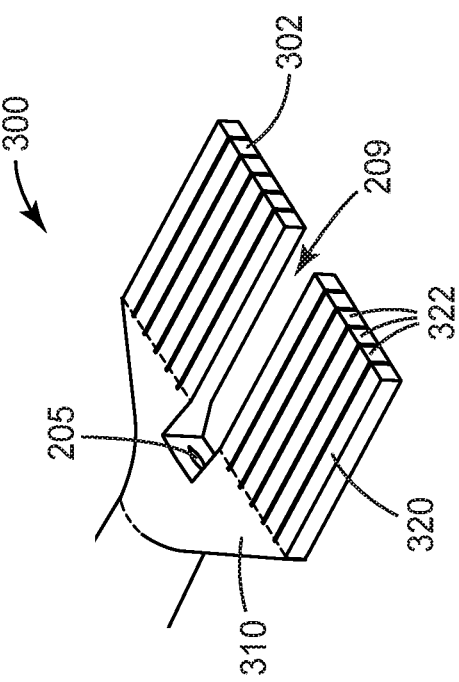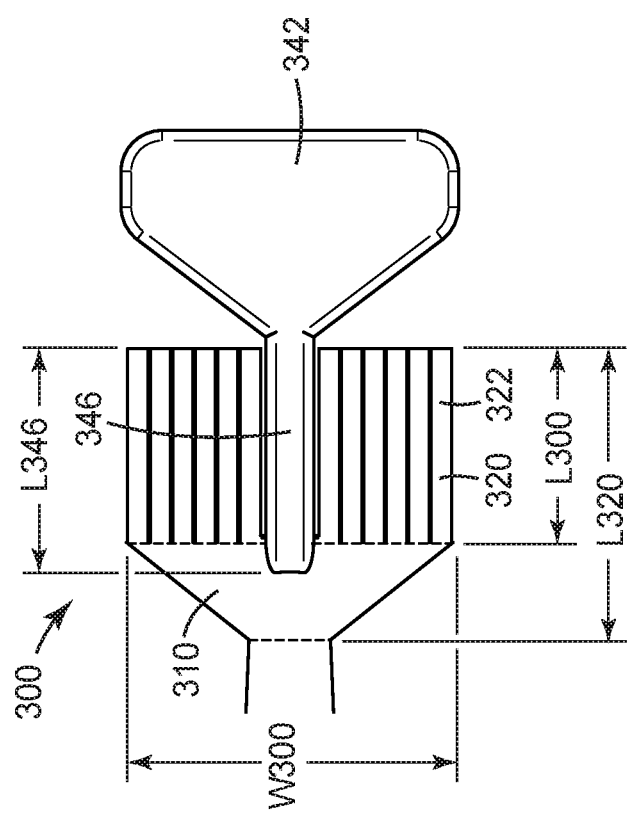

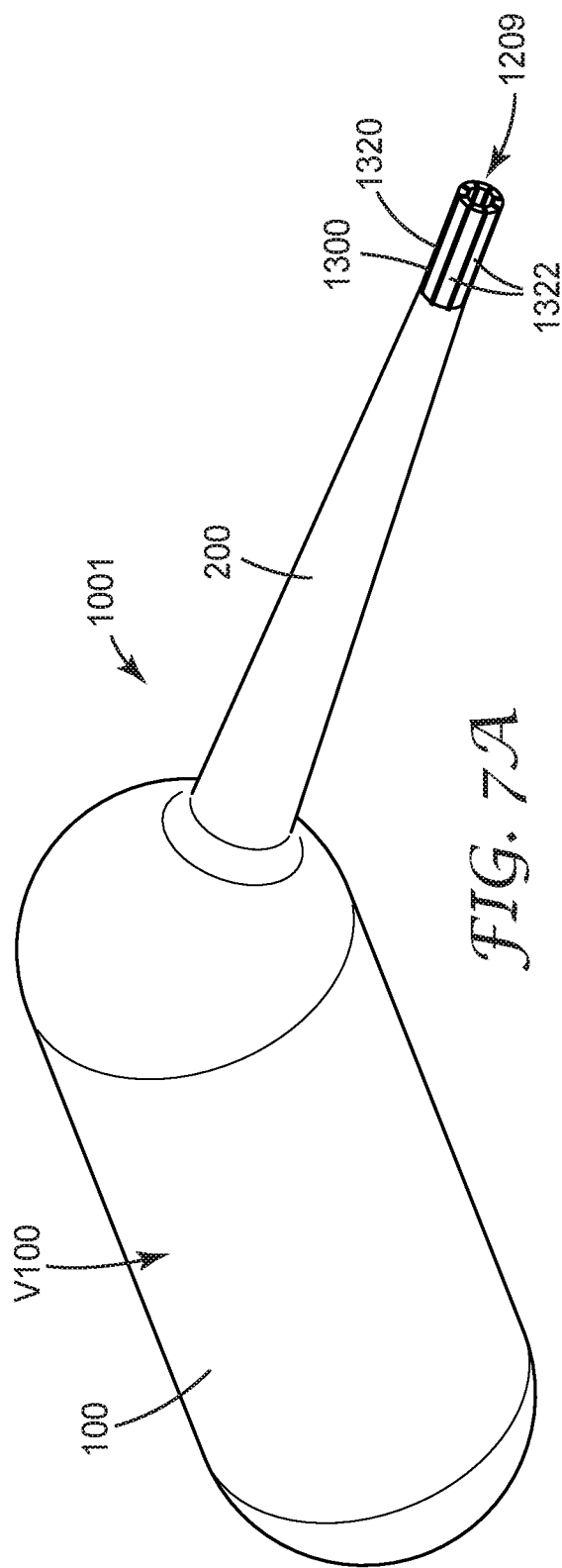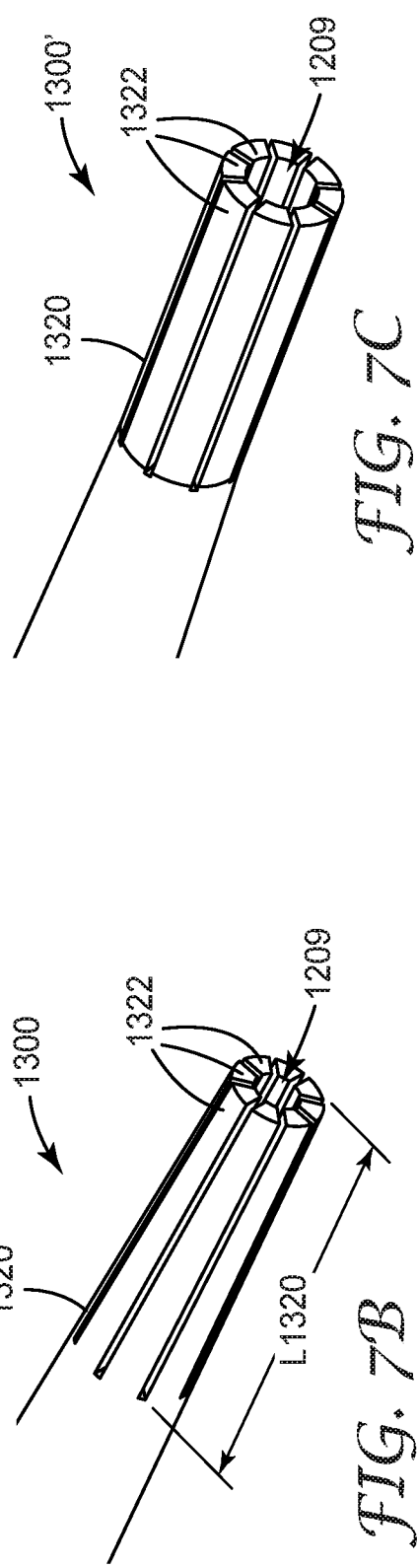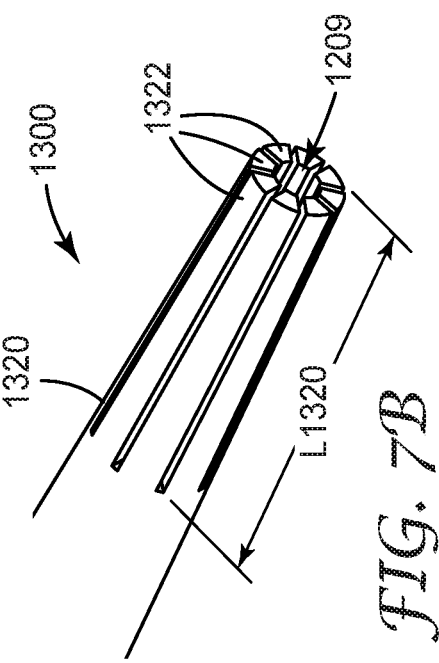

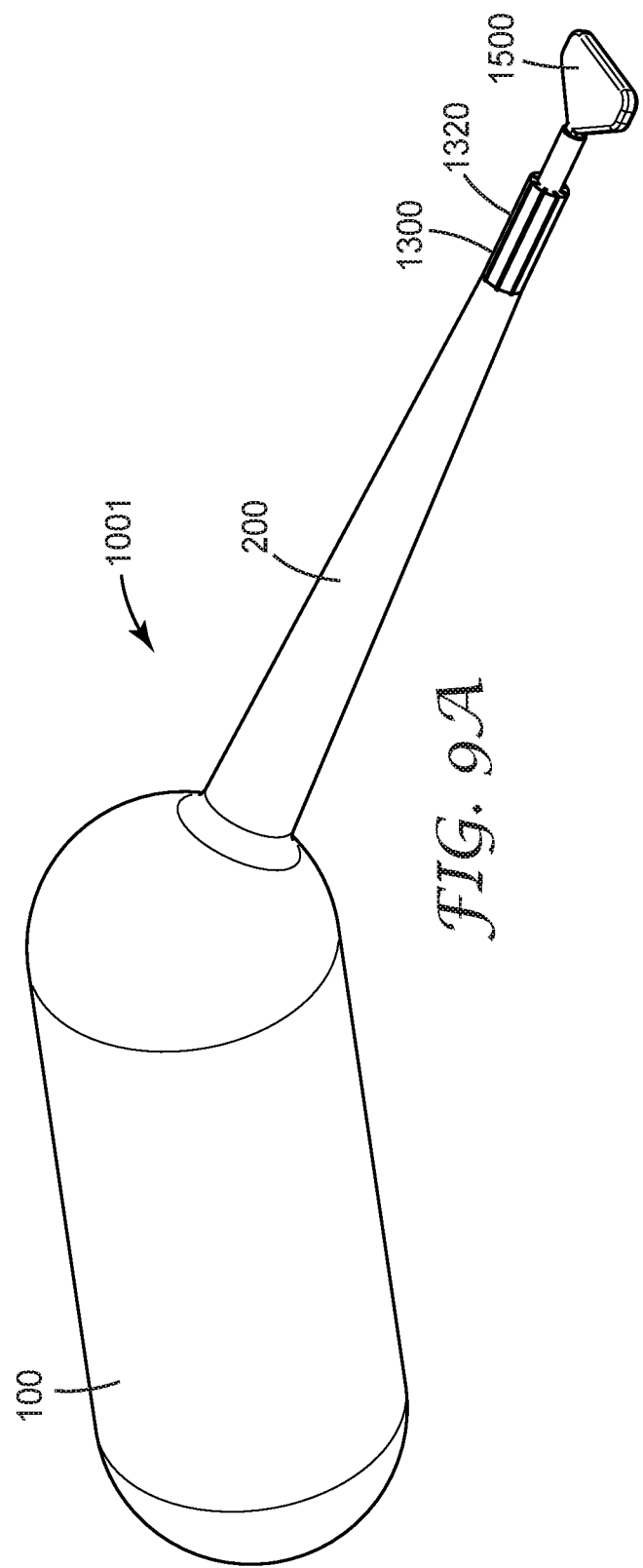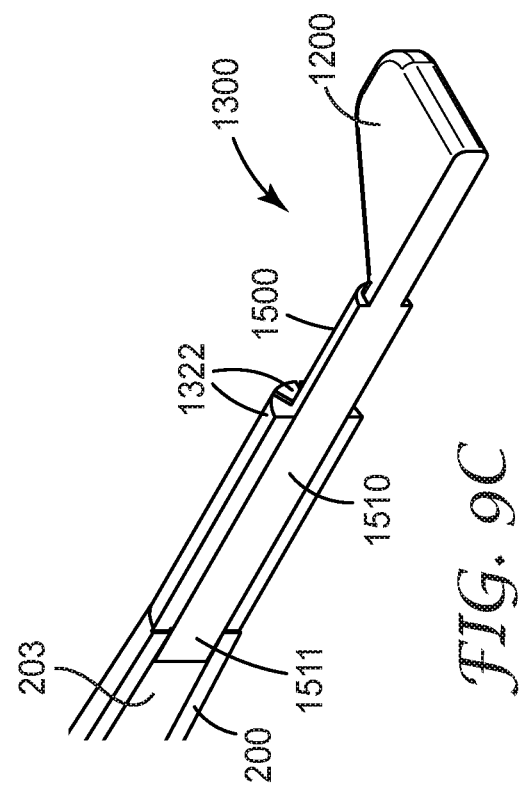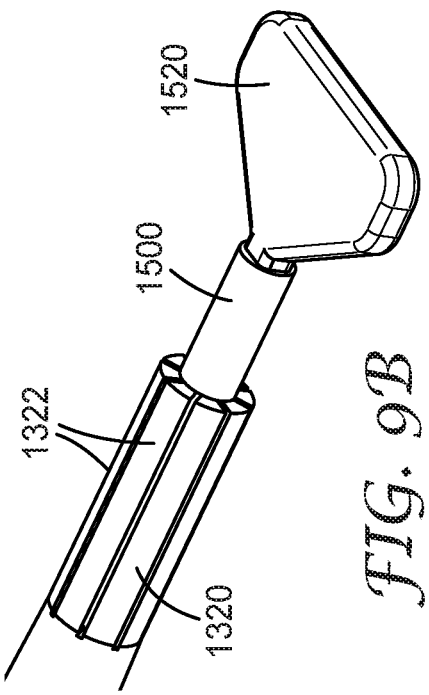

DISPENSER WITH APPLICATOR TIP

FIELD

The present application relates to dispensers suitable for dispensing liquids. In particular, the present disclosure relates to dispensers including a reservoir and an applicator.

BACKGROUND

Plastic ampules and applicators for liquids are known, where the liquid is stored in the ampule and applied using the applicator. However, such ampules typically only include a simple opening that may be provided at the end of an extended nozzle. If the use of an applicator is desired, the applicator is typically provided as a separate element that may be affixed or attached to the ampule or nozzle. Applicators may include, for example, a sponge or a brush.

An example of an ampule with an extended nozzle and an opening at the end of the extended nozzle is provided in U.S. Pat. No. 6,846,459 (Snedden). A similar ampule with a breakable seal at the end of the extended nozzle is provided in U.S. Pat. No. 6,328,715 (Dragan). These ampules are prepared by blow molding from a resilient material. However, the ampule does not include an applicator at the end of the extended nozzle. If an applicator was needed, a separate applicator element would need to be attached to the nozzle. Liquid dispensing applicators with separate applicator components are known, for example, from U.S. Pat. No. 8,899,858 (Margoosian) and U.S. Pat. No. 7,614,811 (Kaufman). However, such applicators made from multiple plastic components are difficult and costly to assemble and have multiple weld seams and joints that are susceptible to failure.

It would be desirable to provide a dispenser for dispensing liquids that includes a liquid reservoir and an applicator.

SUMMARY

The present application relates to dispensers suitable for dispensing liquids. In particular, the present disclosure relates to dispensers including a reservoir and an applicator.

A dispenser for liquids includes a reservoir defining a volume for housing a liquid; a delivery tube comprising a first end attached to the reservoir, and a second end distal from the reservoir, the delivery tube comprising a passage in fluid communication with the volume of the reservoir and extending away from the reservoir; an applicator element comprising an applicator tip and a base attached to the second end of the delivery tube, the applicator tip comprising a plurality of fingers extending away from the base to a distal end of the applicator element distal from the delivery tube; and a removable seal, wherein removal of the removable seal creates an opening in the passage at a location upstream of the applicator tip and a fluid distribution channel between the fingers.

The dispenser may be made by blow molding a reservoir defining a volume for housing a liquid and a delivery tube attached to the reservoir, the delivery tube comprising a proximal end adjacent the reservoir, a distal end extending away from the reservoir, and a passage in fluid communication with the volume of the reservoir, the passage extending from the proximal end to the distal end; adding liquid to the reservoir; and deforming the distal end of the passage to create an applicator. The distal end of the delivery tube may be sealed or closed with a closure. Deforming the distal end may include forming a removable seal.

BRIEF DESCRIPTION OF DRAWINGS

FIG. 3A is a perspective view of an applicator element of a dispenser according to an embodiment.
FIG. 3B is a top view of the applicator element of FIG. 3A.
FIG. 3C is a perspective view of the applicator element of FIG. 3A in an open configuration.
FIG. 7A is a perspective view of a dispenser according to an embodiment.
FIG. 7B is a partial perspective view of an applicator element of the dispenser of FIG. 7A.
FIG. 7C is a partial perspective view of an alternative applicator element of the dispenser of FIG. 7A.
FIG. 9A is a perspective view of the dispenser of FIG. 7A in a sealed configuration according to an embodiment.
FIG. 9B is a partial perspective view of the sealed dispenser of FIG. 9A.
FIG. 9C is a partial cross-sectional view of the sealed dispenser of FIG. 9A.

DETAILED DESCRIPTION

Figure 1A:
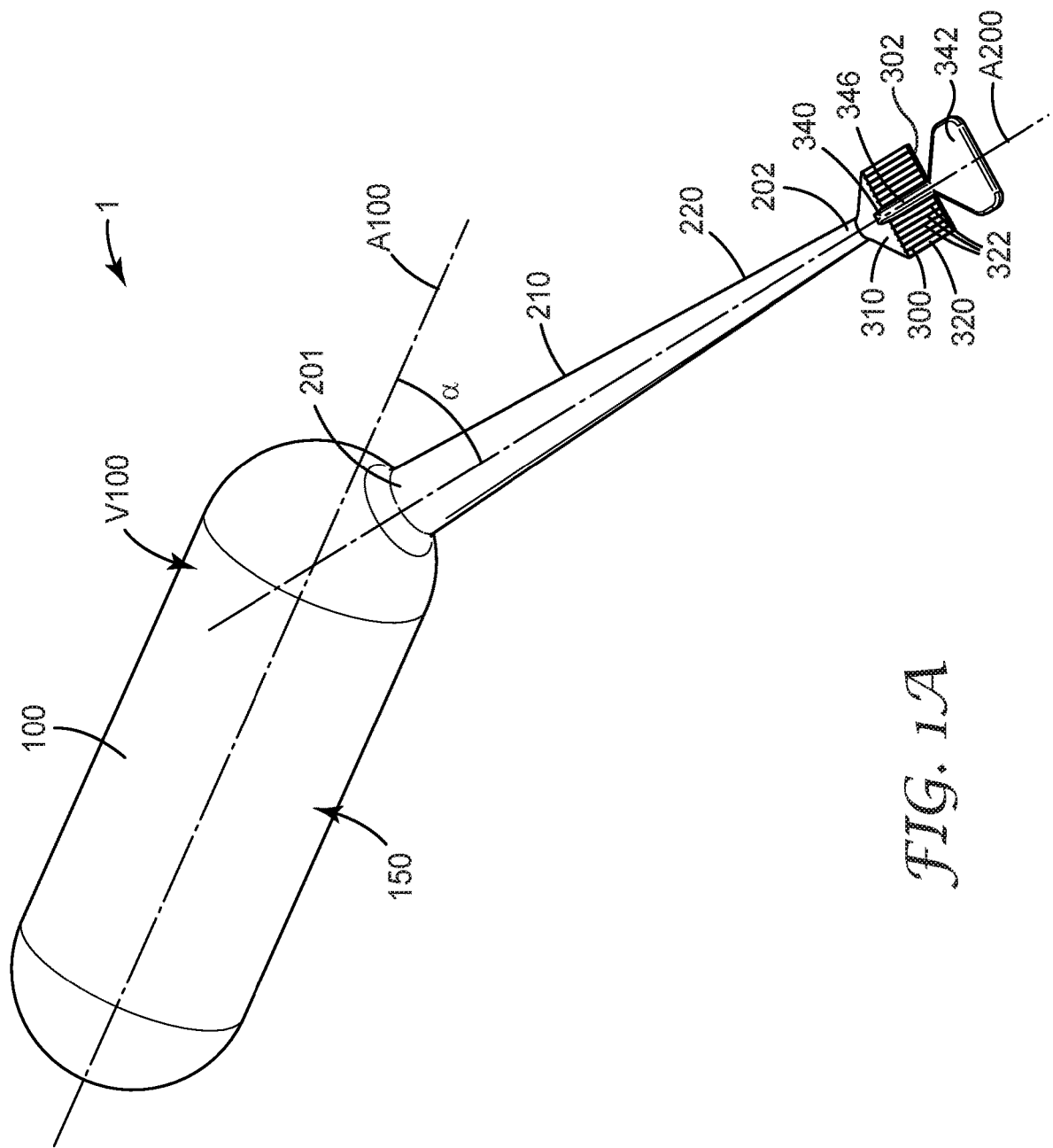
FIG. 1A is a perspective view of a dispenser according to an embodiment.

The present disclosure relates to dispensers suitable for dispensing liquids. In particular, the present disclosure relates to dispensers including a reservoir and an applicator. The dispensers of the present disclosure have particular utility in dental care, oral care, health care, and personal care settings.

The terms "integral" and "integrally formed" are used in this disclosure to describe elements that are formed in one piece (a single, unitary piece) and cannot be separably removed from each other without causing structural damage to the piece.

The term "transparent" is used in this disclosure to describe a material that can be seen through with a naked eye. A transparent material transmits at least 90% of electromagnetic radiation having wavelengths in the ultraviolet to infrared spectrum (e.g., from about 200 nm to about 1400 nm; "UV-IR"). A transparent material may be colorless or colored.

The term "opaque" is used in this disclosure to describe materials that do not allow visible light to pass through. An opaque material transmits less than 10% of electromagnetic radiation having wavelengths in the ultraviolet to infrared spectrum (e.g., from about 200 nm to about 1400 nm; "UV-IR"). An opaque material may be colorless or colored.

The term "translucent" is used in this disclosure to describe a material quality that is between opaque and transparent. For example, it may be possible to see a liquid level through a translucent wall of a container.

The terms "plastic," "polymer" and "polymeric material" refer to materials prepared from one monomer, such as a homopolymer, and to materials prepared from two or more monomers, such as a copolymer, terpolymer, or the like.

The term "about" is used here in conjunction with numeric values to include normal variations in measurements as expected by persons skilled in the art, and is understood have the same meaning as "approximately" and to cover a typical margin of error, such as ±5% of the stated value.

Terms such as "a," "an," and "the" are not intended to refer to only a singular entity, but include the general class of which a specific example may be used for illustration.

The terms "a," "an," and "the" are used interchangeably with the term "at least one." The phrases "at least one of" and "comprises at least one of" followed by a list refers to any one of the items in the list and any combination of two or more items in the list.

As used here, the term "or" is generally employed in its usual sense including "and/or" unless the content clearly dictates otherwise. The term "and/or" means one or all of the listed elements or a combination of any two or more of the listed elements.

The terms "longitudinal" and "axial" are used to refer to a direction or axis that is generally parallel to a central longitudinal axis of an element. The term "longitudinal axis" is used to refer to an axis along the longest dimension of the element.

Relative terms such as proximal, distal, left, right, forward, rearward, top, bottom, side, upper, lower, horizontal, vertical, and the like may be used in this disclosure to simplify the description. However, such relative terms do not to limit the scope of the invention in any way. Terms such as left, right, forward, rearward, top, bottom, side, upper, lower, horizontal, vertical, and the like are from the perspective observed in the particular figure.

The terms "proximal" and "distal" are used to represent directions relative to a user using or holding the dispenser. That is, the term "distal" is used to refer to the direction away from the user and toward the applicator-end of the dispenser; and the term "proximal" is used to refer to the direction toward the user and away from the applicator-end.

According to some embodiments, the dispenser of the present disclosure includes a reservoir, a delivery tube, and an applicator element with an applicator tip. The reservoir, delivery tube, and applicator element may be integrally formed. The dispenser may be initially sealed. The applicator tip is closed with a removable seal or closure that can be removed to create an opening in a passage in the delivery tube.

The dispensers of the present disclosure may, in one or more embodiments, provide a reduction in the number of parts and simplify the fabrication and assembly process by eliminating the need for a secondary or subsequent assembly step, thus lowering manufacturing costs. In addition, the dispensers of the present disclosure, in one or more embodiments, provide a product that is easy and convenient to store and use.

Figure 1B:
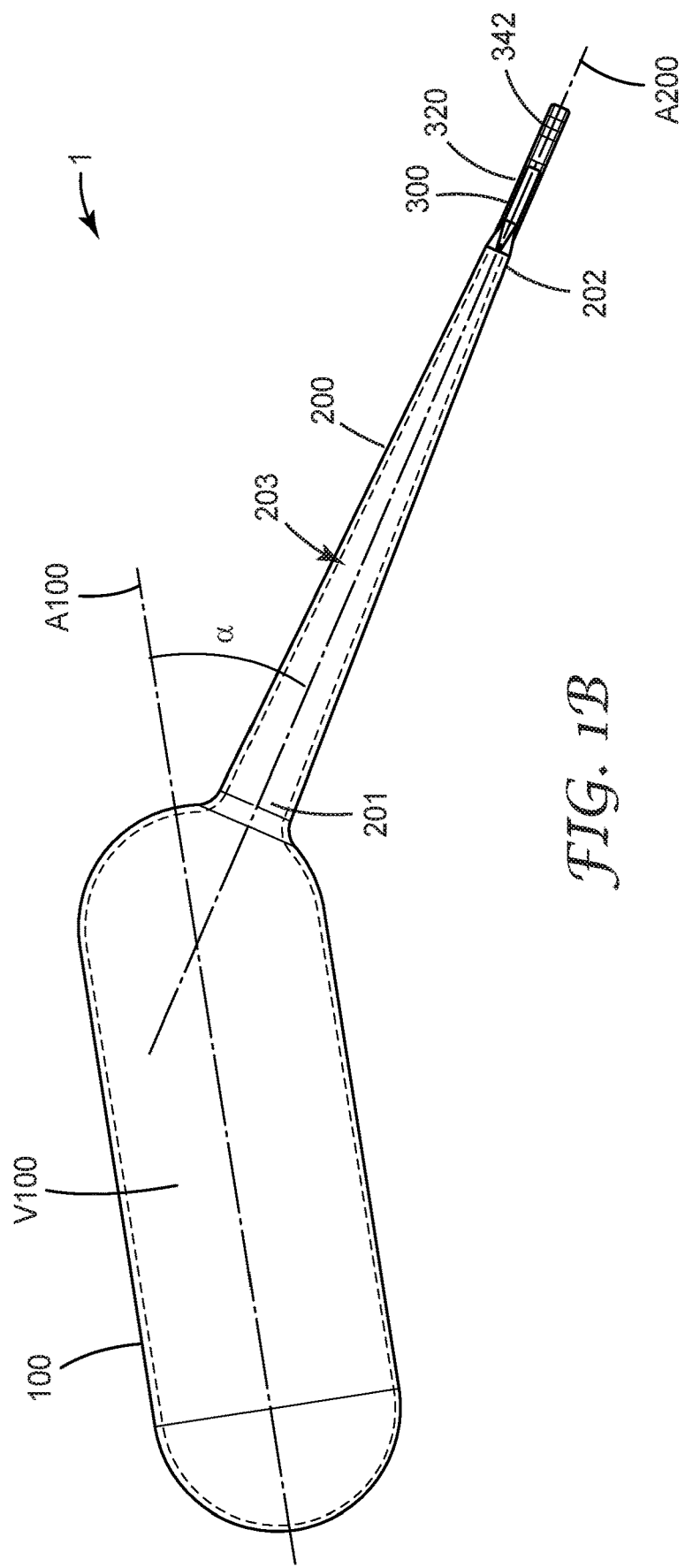
FIG. 1B is a side view of the dispenser of FIG. 1A.
Figure 1C:
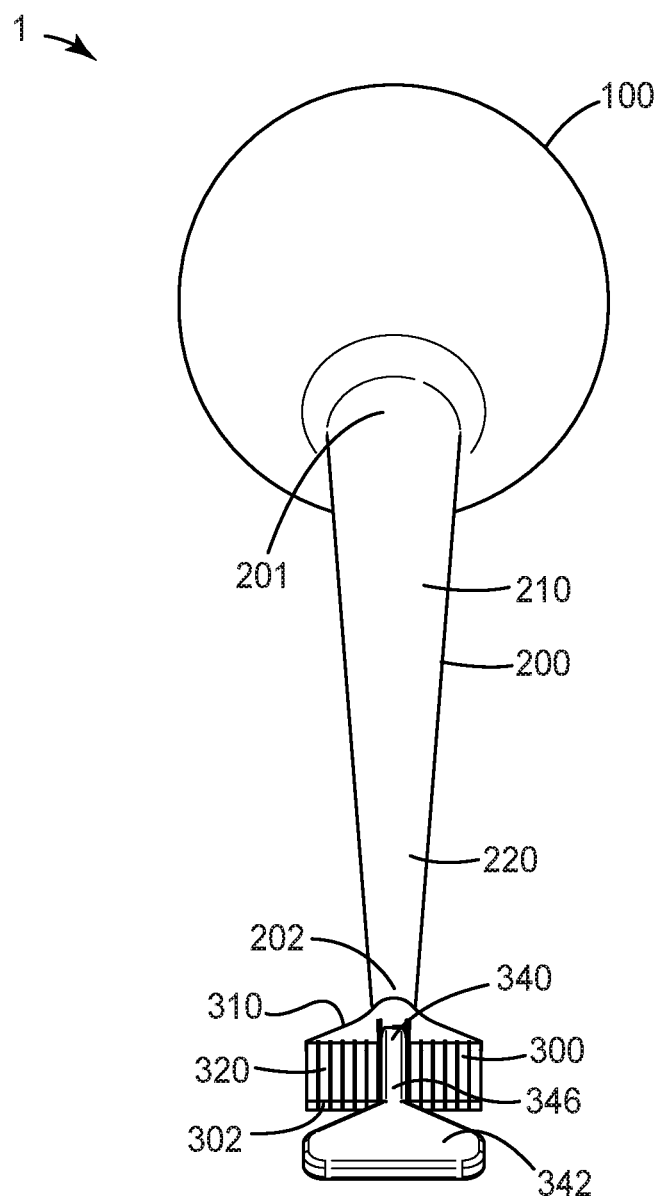
FIG. 1C is an end view of the dispenser of FIG. 1A.

An embodiment of the dispenser 1 is shown in FIGS. 1A-1C. The dispenser 1 includes a reservoir 100 defining a volume V100 for housing a liquid 150, and a delivery tube 200 with a first end 201 attached to the reservoir 100. The delivery tube 200 defines a passage 203 that is in fluid communication with the volume V100 of the reservoir 100. The passage 203 and volume V100 are shown in phantom in FIGS. 1B and 2B. The passage 203 extends between the reservoir 100 and an applicator element 300.

Figure 2A:
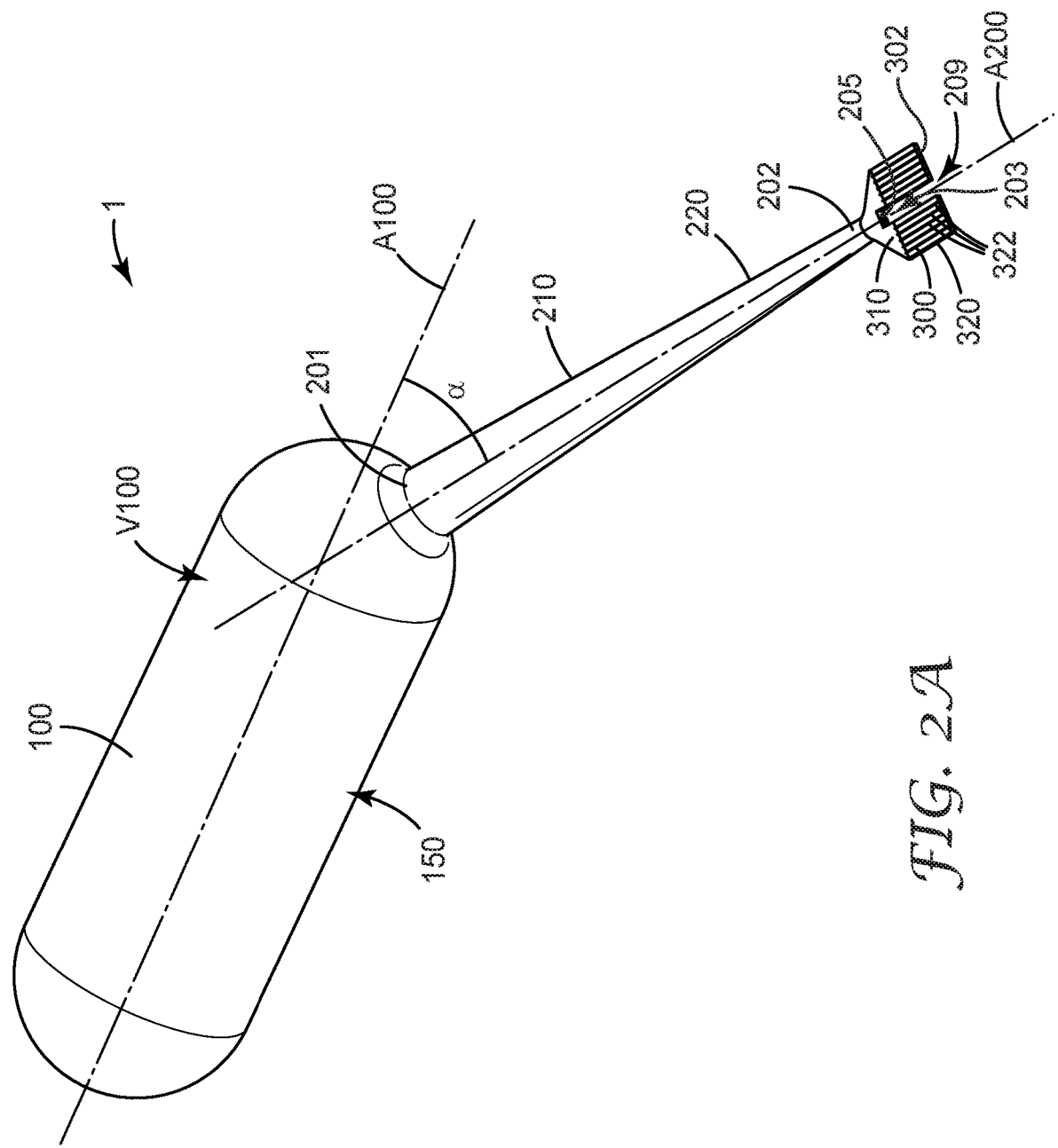
FIG. 2A is a perspective view of the dispenser of FIG. 1A in an open configuration.
Figure 2B:
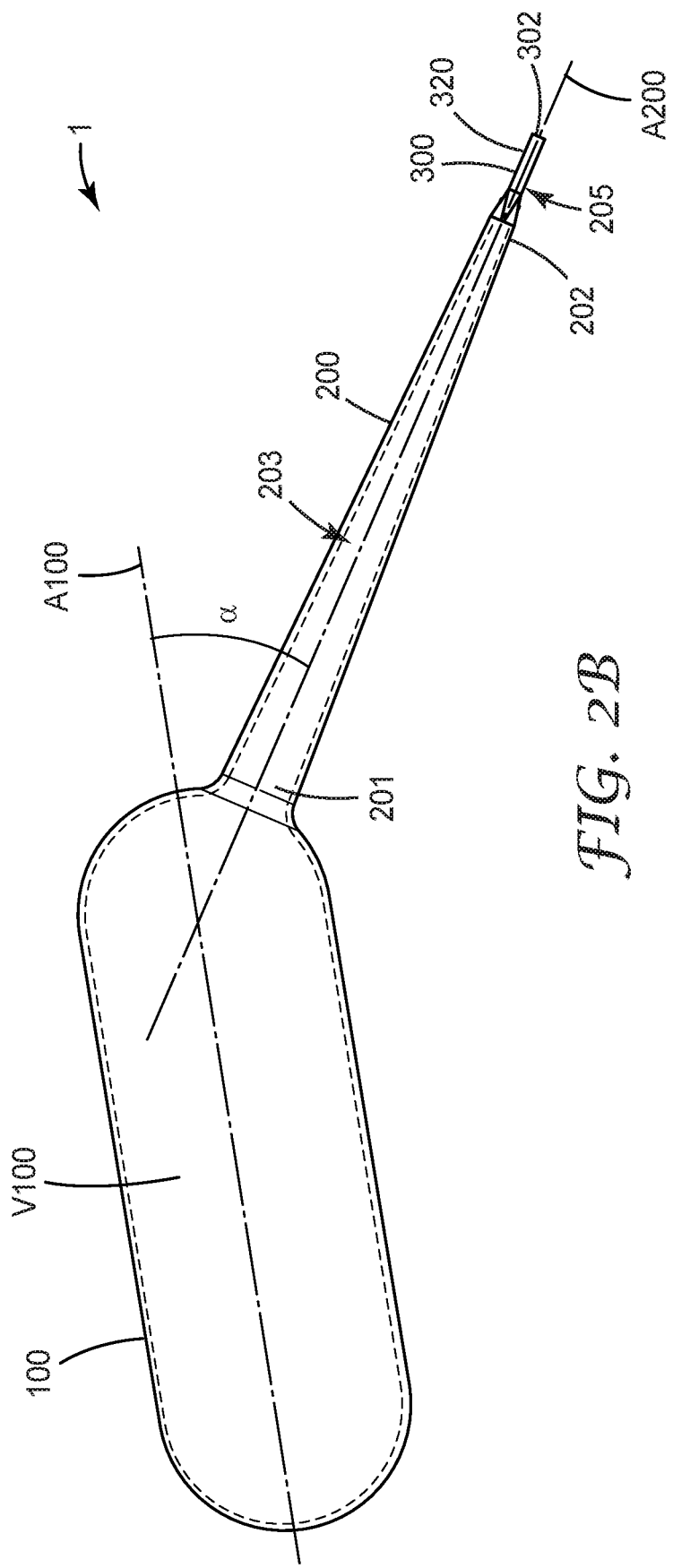
FIG. 2B is a side view of the dispenser of FIG. 2A.
Figure 2C:
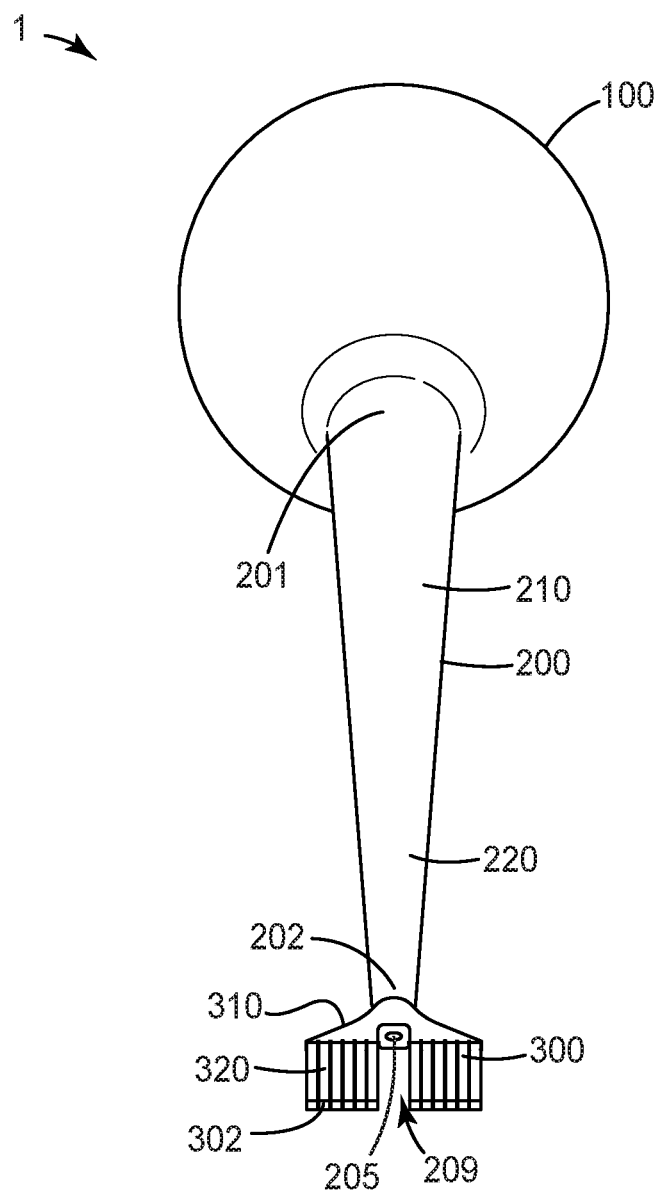
FIG. 2C is an end view of the dispenser of FIG. 2A.

The applicator element 300 includes an applicator tip 320 and a base 310 attached to the second end 202 of the delivery tube 200 such that the applicator tip 320 extends away from the base 310 to a distal end 302 of the applicator element 300 distal from the delivery tube 200. The dispenser 1 further includes a removable seal 340. Removal of the removable seal 340 creates an opening 205 in the passage 203. According to an embodiment, the opening 205 forms at a location upstream of the applicator tip 320. FIGS. 2A-2C show the dispenser 1 of FIGS. 1A-1C in an open configuration, where the removable seal 340 has been removed, leaving an opening 205 at the distal end of the delivery tube 200.

In at least some embodiments, the dispenser 1, including the reservoir 100, the delivery tube 200, the applicator element 300, and the removable seal 340, is integrally formed. In some embodiments, the reservoir 100, the delivery tube 200, and the applicator element 300 are integrally formed. The dispenser 1 may be formed by blow molding, where the delivery tube 200, the applicator, and the removable seal 340 are formed from an integrally formed molded article. In one embodiment, the applicator element 300 and the removable seal 340 are integrally formed to the delivery tube 200. In another embodiment, the delivery tube 200 is integrally formed to the reservoir 100. In one embodiment, the base 310 of the applicator element 300 and the removable seal 340 are integrally formed. Alternatively, the removable seal 340 may be formed from a separate piece and attached to the applicator element 300 (e.g., the base 310) in a subsequent step. The applicator tip 320 may be integrally formed with the base 310, or may be made separately and attached to the base 310.

The dispenser 1 can house a liquid 150 within the reservoir 100. The type of liquid is not particularly limiting, as the dispenser 1 may be useful for dispensing various types of liquids. The dispenser 1 may be particularly useful for housing and dispensing liquids that are used or dispensed at relatively small volumes, for example at typical unit dose volumes in a dental care, oral care, health care, or personal care setting. In embodiments where the dispenser 1 is sealed, the dispenser 1 may be used to house a sterile liquid. Thus, the dispenser 1 may be particularly useful for housing and dispensing sterile, single dose liquids. The dispenser 1 may also be useful for housing and dispensing liquids that are applied to a relatively small area and/or that require some degree of precision in their application.

Some examples of liquids that can be disposed in the reservoir 100 and dispensed with the dispenser 1 include compositions used in dental care, oral care, health care, and personal care. For example, the dispenser 1 can be used to house and dispense various dental care liquids, such as fluoride treatments, whitening treatments, color cosmetics, calculus softening agents, and oral malodor treatments.

According to an embodiment, the dispenser 1 is a disposable. The dispenser 1 is closed by a removable seal such that by removing the removable seal, an opening 205 is created in the passage 203 extending from the reservoir 100 to the applicator element 300. According to some embodiments, the dispenser 1 is not intended to be re-sealed after the seal has been removed and the opening 205 created.

The volume V100 of the reservoir 100 can be selected to be suitable for the intended purpose. For example, the reservoir 100 may have a volume V100 of about 0.1 mL to about 100 mL, or about 1 mL to about 5 mL. In one exemplary embodiment, the volume V100 is about 1.5 mL to about 3 mL.

The material of the dispenser 1 may be selected to be compatible with its intended use. For example, the dispenser 1 may be made of a resilient material and have a suitable wall thickness that accommodates breaking and/or removal of the removable seal 340 and dispensing the liquid 150 from the reservoir 100. The dispenser 1 and, in particular, the delivery tube 200 have sufficient strength and rigidity to enable twisting, turning, or bending the removable seal 340 (e.g., the removable tab) to break or remove the removable seal 340. The dispenser 1 and, in particular, the reservoir 100 have sufficient resiliency and flexibility to enable manually squeezing the reservoir 100 to push the liquid into the passage 203 and through the opening 205. The material of the dispenser 1 is preferably also compatible with the liquid stored in the reservoir 100 and provides a sufficient barrier between the liquid and the ambient conditions outside of the dispenser 1. In some embodiments, the dispenser 1 is made from a polymer, such as polyolefins, polyethylene, polypropylene, ethylene/propylene copolymer, polyester, polyamide, polyacrylate, polystyrene, or a combination thereof.

The reservoir 100 or a part of the reservoir 100 may be made of a transparent or translucent material so that the amount of liquid in the reservoir 100 can be observed visually. Alternatively, the reservoir 100 or a part of the reservoir 100 may be made of an opaque material that facilitates printing information on the wall of the reservoir 100, such as information about the contents, manufacturer, use, safety, expiration, etc. In some embodiments, the reservoir 100 is made from a polymer, such as polyolefins, polyethylene, polypropylene, ethylene/propylene copolymer, polyester, polyamide, polyacrylate, polystyrene, or a combination thereof. The reservoir 100 may have a wall thickness of at least about 0.15 mm, at least about 0.2 mm, at least about 0.4 mm, at least about 0.5 mm, or at least about 0.6 mm. In some embodiments, the wall thickness may be up to about 1 mm, up to about 0.9 mm, or up to about 0.8 mm.

The reservoir 100 may have any suitable shape. Exemplary shapes of the reservoir 100 are shown in the figures. For example, in some embodiments the reservoir 100 has an elongated or oblong body with a generally oblong or obround cross-sectional shape along the longitudinal axis. The transverse cross section of the reservoir 100 may be round, oval, or obround. However, other shapes are also possible, including shapes that are more or less rounded, include corners, or have one end that is narrower than the other.

The shape and orientation of the delivery tube 200 may also be designed such that they facilitate dispensing of the liquid 150 from the dispenser 1. For example, the delivery tube 200 (e.g., a longitudinal axis A200 of the delivery tube 200) may be disposed at an angle α relative to the reservoir 100. In one embodiment, at least a distal portion 220 of the delivery tube 200 is at an angle α relative to the reservoir 100. The angle α may be from about 0° to about 90°, from about 30° to about 60°, or from about 40° to about 50°. In one embodiment, the delivery tube 200 or at least a distal portion 220 of the delivery tube 200 is at an angle α of about 45°. The entire delivery tube 200 may be angled, as shown, or the delivery tube 200 may have a bend such that a proximal portion 210 of the delivery tube 200 is aligned with the longitudinal axis A100 of the reservoir 100, and the distal portion 220 is at angle α relative to the proximal portion 210.

In some embodiments, the delivery tube 200 may also be formed with a portion that has circumferential pleating or an accordion-type folding (not shown) that facilitates the adjustable bending, flexing, or displacing of the delivery tube 200 from a first angle α relative to the reservoir 100 longitudinal axis A100 to a second angle α' (not shown) relative to the longitudinal axis A100 of the reservoir. In such embodiments the angle α of tube 200 relative to the reservoir may be easily adjusted and tube 200 stays in the new position, until adjusted again, if needed.

The delivery tube 200 may be tapered such that the second (distal) end 202 of the delivery tube 200 is narrower than the first (proximal) end 201. For example, the delivery tube 200 may have a first cross section taken transverse to the longitudinal axis A200 of the delivery tube 200 at a first location that is larger than a second cross section taken transverse to the longitudinal axis A200 of the delivery tube 200 at a second location distal to the first location. The width at the second cross section may be from about 10% to about 75%, or from about 20% to about 50% of the width at the first cross section. The tapering may also narrow the passage 203 such that the cross section of the passage 203 at the second (distal) end 202 is smaller than at the first (proximal) end 201. The tapering may begin at the first (proximal) end 201 or somewhere between the first and second ends 201, 202 and may continue all the way to the second end 202, or end before the second end 202.

The delivery tube 200 defines a passage 203 that connects the reservoir 100 to the applicator element 300. When the removable seal 340 is in place (e.g., has not been broken or removed), the passage is closed, and the liquid 150 in the reservoir 100 cannot flow to the applicator element 300. However, after the removable seal 340 has been broken or removed, an opening 205 is created adjacent the distal end of the passage 203. The size of the passage 203, the removable seal 340 and thus the opening 205 can be constructed to accommodate the liquid 150 in the reservoir 100. For example, the passage 203 and the opening 205 can be made larger for a more viscous liquid, and smaller for a less viscous liquid.

While the size of the passage 203 and the opening 205 may be adjusted to accommodate liquids with varying viscosities, it may be desirable to select the viscosity of the liquid 150 such that it can be conveniently dispensed from the dispenser 1. Suitable viscosities may range from about 0.5 Pa·s to about 500 Pa·s, from about 1 Pa·s to about 400 Pa·s, from about 5 Pa·s to about 300 Pa·s, or from about 10 Pa·s to about 200 Pa·s, at a shear rate of 1.0/s.

In one embodiment, the liquid has a viscosity of about 5 to about 300 Pa·s at a shear rate of 1.0/s, and the passage 203 in the distal portion 220 of the delivery tube 200 and the opening 205 are sized to accommodate the viscosity of the liquid. For example, the opening 205 may have a cross dimension of about 0.1 mm to about 4 mm, about 2 mm to about 3 mm, about 0.25 mm to about 2 mm, or about 0.4 mm to about 1.5 mm. The opening 205 may have a cross sectional area (perpendicular to the longitudinal axis of the delivery tube 200) may range from about 0.008 mm$^2$ to about 12.5 mm$^2$. In some embodiments, the opening 205 may have any suitable cross-sectional shape, for example circular, oval, square, triangular, rectangular, or any regular or irregular polygonal or non-polygonal shape. The shape of the opening 205 may be selected to optimize the flow of liquid 150 to the fluid distribution channel 209 within the applicator tip 320 (e.g., between the plurality of fingers).

At the distal end of the delivery tube 200, the dispenser 1 includes an applicator element 300. Enlarged views of various applicator elements 300 are shown in FIGS. 3A-6B. The applicator element 300 includes a base 310 that is integrally attached to the second end 202 of the delivery tube 200. An applicator tip 320 extends distally from the base 310. In some embodiments, the applicator tip 320 includes two or more fingers 322 that create a brush-like extension of the applicator element 300.

Various possible shapes of the applicator element 300 are shown in the figures. For example, in some embodiments the applicator element 300 is a substantially flat extension that includes a substantially triangular base 310 and a plurality of fingers 322 that extend distally in the same plane as the base 310. The applicator tip 320 may include a suitable number of fingers 322, such as up to 20 fingers 322, up to 10 fingers 322, or up to 6 fingers 322. However, other shapes are also possible, including shapes that are longer, shorter, wider, narrower, more or less rounded, thicker, or include more or fewer fingers (see, for example, the alternative configurations shown in FIGS. 5A and 5B), or more three-dimensional elements (see, for example, the alternative configurations shown in FIGS. 6A, 6B, 7A, and 7B).

The applicator element 300 is shown as disposed generally parallel to the longitudinal axis A200 of the delivery tube 200 and perpendicular to a plane defined by the longitudinal axis of the reservoir 100 and the longitudinal axis of the delivery tube 200. However, other angular positions of the applicator element 300 are possible (e.g., the applicator element 300 may have a rotational angle other than 90° relative to the plane defined by the longitudinal axis of the reservoir 100 and the longitudinal axis of the delivery tube 200). Further, the applicator tip 320 may be angled relative to the applicator base 310. For example, the applicator tip 320 may be disposed at an angle of about 0° to about 90°, or about 0° to about 30° relative to the applicator base 310.

The applicator element 300 may have any suitable size. For example, the applicator element 300 may be sized to accommodate the viscosity of the liquid 150 housed in the reservoir and/or the intended use of the liquid 150. In some embodiments it may be desirable to have a larger applicator element 300, or an applicator element 300 that is thicker and has less flexibility. In other embodiments, it may be desirable to have a smaller applicator element 300, or one that is thinner and has more flexibility. In one embodiment, the applicator element 300 has a length L300 of about 3 mm to about 25 mm, or about 4 mm to about 15 mm. The applicator element 300 may also have a width W300 of about 1 mm to about 20 mm, about 2 mm to about 12 mm, about 3 mm to about 10 mm. In one embodiment, the applicator tip 320 has a length L320 of about 1 mm to about 20 mm, about 2 mm to about 10 mm, or about 3 mm to about 6 mm. The applicator element 300 may have a thickness that varies from the distal end of the delivery tube 200, where the applicator element may be thicker, to the distal end of the applicator tip 320, where the applicator element may have the same thickness as the applicator tip 320. The thickness of the applicator element 300 may be the same in the area of the applicator tip 320 as at the base 310, or the applicator tip 320 may be thinner than the base 310 to create a more flexible applicator tip 320. The individual fingers of the applicator tip 320 may range in thickness from about 0.1 mm to about 2 mm, about 0.2 mm to about 1.5 mm, or about 0.3 mm to about 1 mm.

In some embodiments, the applicator element 300 includes fingers that can be splayed upon use and the applicator element 300 may have a use width that is greater than the width W300 prior to use. For example, an applicator element 300 with a width W300 of about 2 mm may have a use width of about 4 mm.

The dispenser 1 includes a removable seal 340 that can be removed to create an opening 205 adjacent the second (distal) end 202 of the delivery tube 200. According to an embodiment, the opening 205 is upstream of the applicator tip 320. In some embodiments, the opening 205 is upstream of the entire applicator element 300.

The removable seal 340 may include a removable tab 342. In some embodiments, the removable tab 342 extends distally beyond the applicator tip 320. The removable tab 342 may be connected to the passage 203 by a breakable extension 346. When the removable seal 340 is broken or removed, the removable tab 342 and the breakable extension 346 are removed such that the passage 203 at the second (distal) end 202 of the delivery tube 200 is exposed, creating the opening 205, as seen, for example, in FIGS. 3C, 4C, 5B, and 6B. Removal of the removable seal 340 may also create a fluid distribution channel 209 within the applicator tip 320 (e.g., between the plurality of fingers).

Figure 4A:
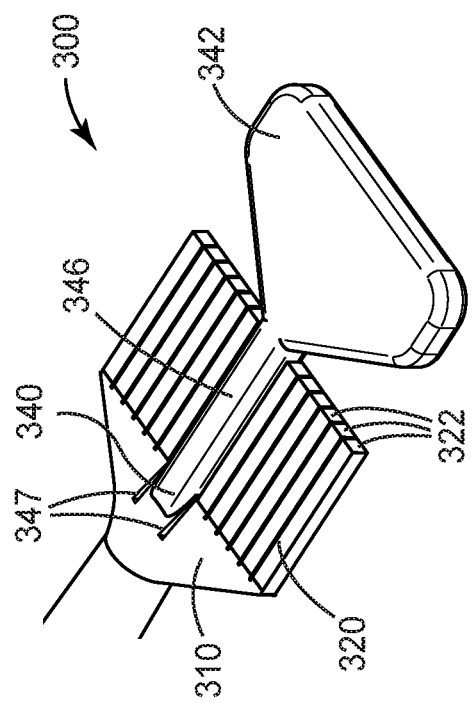
FIG. 4A is a perspective view of an applicator element of a dispenser according to an embodiment.
Figure 4C:
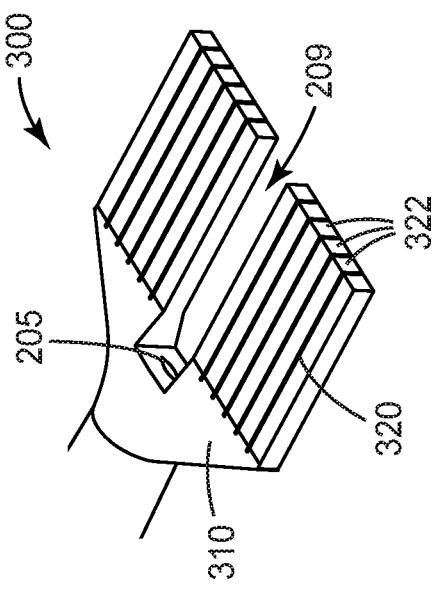
FIG. 4C is a perspective view of the applicator element of FIG. 4A in an open configuration.
Figure 4B:
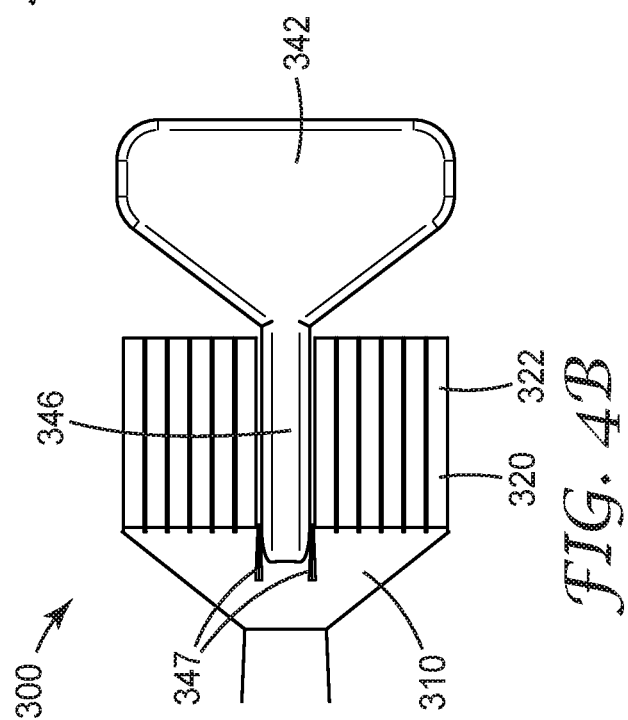
FIG. 4B is a top view of the applicator element of FIG. 4A.
Figure 5B:
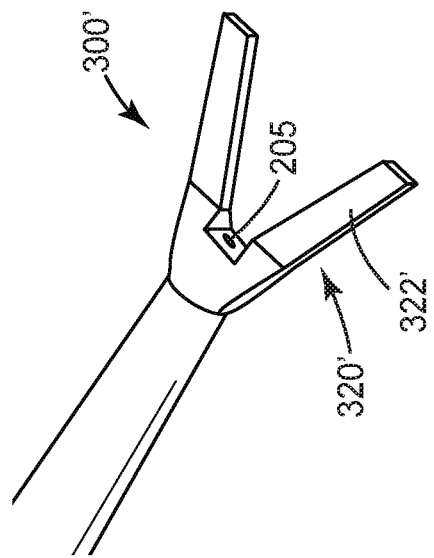
FIG. 5B is a perspective view of the applicator element of FIG. 5A in an open configuration.
Figure 5A:
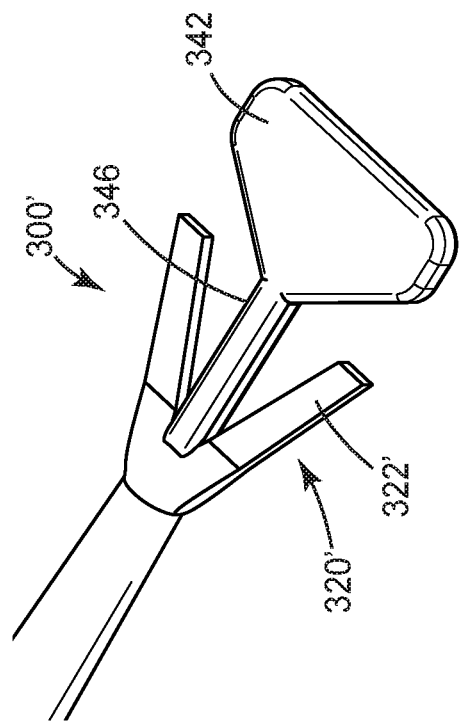
FIG. 5A is a perspective view of an applicator element of a dispenser according to an embodiment.

The applicator element 300 may further include cuts 347 extending proximally into the base 310 at the sides of the breakable extension 346 as seen in FIGS. 4A-4C. The cuts 347 may facilitate easy separation of the breakable extension 346.

The removable tab 342 and the breakable extension 346 may have any suitable shape and size. For example, the removable tab 342 may be substantially flat, and may be disposed generally in the same plane as the applicator tip 320. The breakable extension 346 may be a cylindrical element that has a length L346 that is longer than the length L320 of the applicator tip 320. The breakable extension 346 may begin upstream of the applicator tip 320, and may extend distally at least part of the length of the applicator tip 320 or may extend to or beyond the distal end of the applicator tip 320. In the Figures show, the removable tab 342 and the breakable extension 346 are centered between two halves of the applicator tip 320, and the two halves of the applicator tip 320 are symmetrical about the breakable extension 346. However, other shapes and configurations can be used, such as where the removable tab 342 and the breakable extension 346 are not centered (e.g., where the breakable extension 346 is angled), and/or where the applicator tip 320 is asymmetrical.

FIGS. 5A-5B and 6A-6B demonstrate alternative configurations of the applicator element 300', 300". In an embodiment shown in FIGS. 5A and 5B, the applicator tip 320' includes two fingers 322' that extend distally at an angle away from a longitudinal axis of the delivery tube 200. The removable tab 342 and the breakable extension 346 extend distally between the two fingers 322'.

Figure 6B:
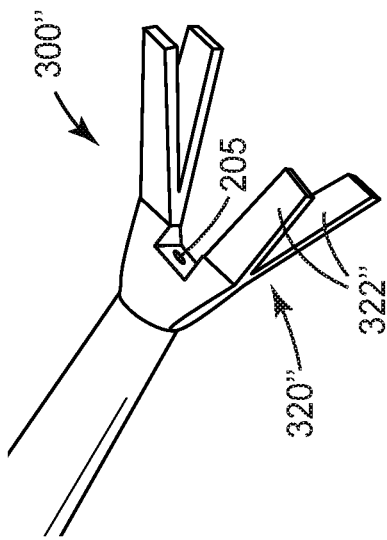
FIG. 6B is a perspective view of the applicator element of FIG. 6A in an open configuration.
Figure 6A:
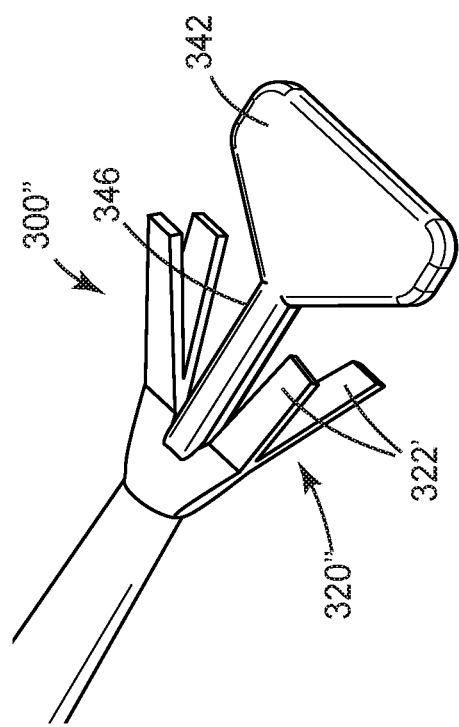
FIG. 6A is a perspective view of an applicator element of a dispenser according to an embodiment.

In an embodiment shown in FIGS. 6A and 6B, the applicator tip 320" includes two sets of two fingers 322" that extend distally at an angle away from a longitudinal axis of the delivery tube 200. On each side of the longitudinal axis, two fingers 322" are stacked or layered such that one finger 322" overlays another. The removable tab 342 and the breakable extension 346 extend distally between the fingers 322".

FIGS. 7A-7C demonstrate alternative configurations of the dispenser 1001 and the applicator element 1300. The applicator element 1300 may include an applicator tip 1320 that extends from the distal end of the delivery tube 200. The applicator tip 1320 may include a plurality of fingers 1322 that are disposed concentrically about the fluid distribution channel 1209. The fingers 1322 may extend distally from the distal end of the delivery tube 200.

Figure 8A:
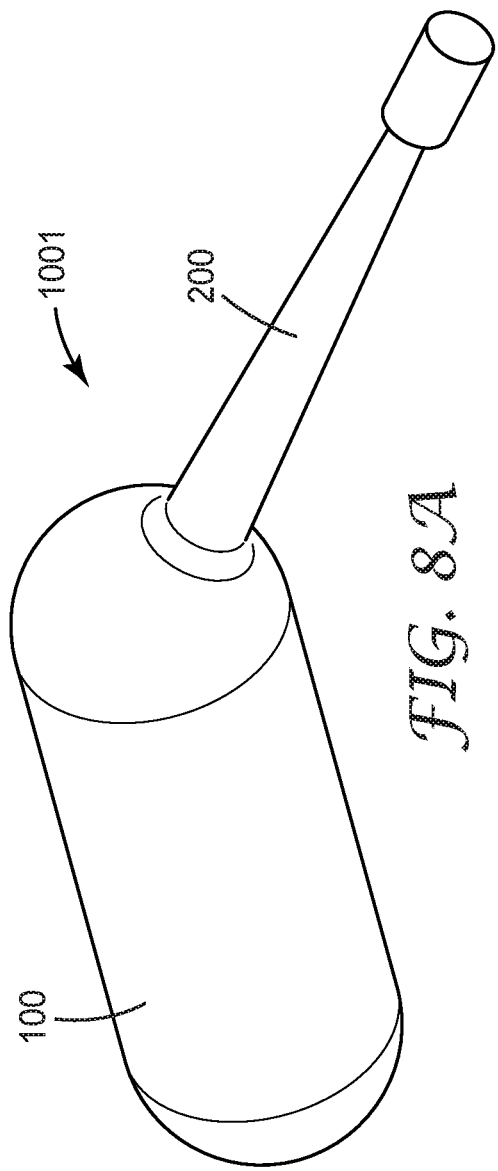
FIG. 8A is a perspective view of the dispenser of FIG. 7A in a sealed configuration according to an embodiment.
Figure 8C:
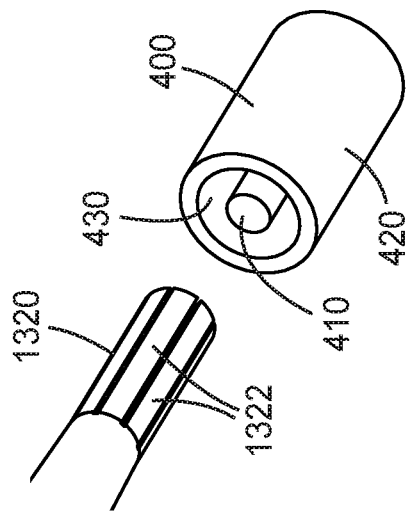
FIG. 8C is a partial exploded view of the sealed dispenser of FIG. 8A.
Figure 8B:
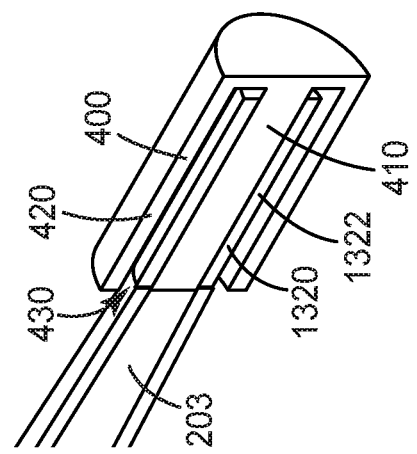
FIG. 8B is a partial cross-sectional view of the applicator element and closure of FIG. 8A.

The passage 203 of the dispenser 1001 of FIGS. 7A-7C may be closed by a closure 400, 1500, as shown in FIGS. 8A, 8B, and 9A-9C. In the embodiment shown in FIGS. 8A-8C, the closure 400 is a cap that includes a plug 410. For example, the closure 400 may include a cylindrical plug 410 extending at the center of the closure 400. The closure 400 may further include a cylindrical outer sleeve 420. The sleeve 420 and the plug 410 define a gap 430 that can accommodate the applicator tip 1320. When the closure 400 is placed over the applicator tip 1320, the proximal end of the plug 410 extends partially into the passage 203 of the delivery tube 200 to close the passage 203. The closure 400 may also be sealed (e.g., heat sealed) onto the end of the delivery tube 200. For example, the proximal end of the plug 410 may be sealed (e.g., heat sealed) onto the distal end of the passage 203.

An alternative closure is shown in FIGS. 9A-9C. As shown in the figures, the passage 203 of the dispenser 1001 may be closed by a closure 1500. The closure 1500 includes a cylindrical plug 1510 constructed to extend partially into the delivery tube 200, and a tab portion 1520. When the plug 1510 is inserted into the delivery tube 200, the proximal portion 1511 of the plug 1510 fits inside the passage 203 of the delivery tube 200 to close (e.g., seal) the passage 203. The tab portion 1520 may extend distally from the plug 1510 to provide a grip for removing and/or replacing the closure 1500. The closure 1500 may also be sealed (e.g., heat sealed) onto the end of the delivery tube 200. For example, the proximal end of the plug 1510 may be sealed (e.g., heat sealed) onto the distal end of the passage 203.

The dispensers of the present disclosure can be made by any suitable method by which the desired shape and configuration of the dispenser can be achieved. According to some embodiments, the dispenser may be made by blow molding. For example, a so-called blow-fill-seal ("BFS") method can be used to both make and fill the dispenser, and to seal the liquid-filled dispenser. Blow-fill-seal (BFS) is a manufacturing process where a container system is molded and filled in the same molding machine. BFS uses a combination of negative and positive pressure (e.g., vacuum and blow molding) to form the geometry of a part without any internal mold cores, along with liquid filling to fill the part with a liquid composition. The liquid can be sterile and can be added into the container aseptically. BFS-molded containers eliminate the need for container caps or closures since the finished product is one unitary part with an integrated closure system.

The BFS method may include providing a heated parison of a polymeric material from which the dispenser 1 will be formed. The reservoir and delivery tube may be molded out of any suitable moldable material, such as polyolefins, polyethylene, polypropylene, ethylene/propylene copolymer, polyester, polyamide, polyacrylate, polystyrene, or a combination thereof.

The BFS molding process may include using a mold defining a negative of a desired outer shape of the dispenser 1. Such a mold can include a pair of mating mold halves, and can include a negative of at least a portion of the dispenser 1, including the reservoir 100 and the delivery tube 200 or a pre-form of the delivery tube 200 that may be formed into the delivery tube 200 later in the process. According to an embodiment, the dispenser 1 is made by first blow molding a reservoir 100 defining a volume V100 for housing a liquid and a delivery tube 200 integrally attached to the reservoir. The delivery tube 200 includes a passage 203 extending away from the reservoir 100. The passage is in fluid communication with the volume of the reservoir. The pre-form of the delivery tube 200 may also include a pre-form of the applicator element 300 that may be formed into its final shape in a subsequent step, e.g., during or after the sealing step.

During the BFS molding process, a gas can be injected into the heated parison in order to effect blow molding of the polymeric material to form at least a portion of the dispenser 1 having an open end. Subsequently and/or simultaneously, negative pressure can be applied to the outside of at least a portion of the parison in to form the reservoir 100 and at least a portion of the delivery tube 200. A liquid may then be added into the still open-ended reservoir 100, for example by inserting a nozzle or needle through the opening or passage. The reservoir may be filled partially or fully. In some embodiments, the liquid is added in a sterile or aseptic step (e.g., sterile filled). The method may further include adding another liquid or other ingredients (liquid, solid, or gas) into the reservoir.

The distal end of the delivery tube may be sealed by melting and pressing together the distal portion of the pre-form of the delivery tube 200 to close the dispenser. The contents of the sealed dispenser may be sterile, and/or may be further sterilized in a subsequent sterilizing step. The sealed distal end of the delivery tube may be deformed to create an applicator element and a removable seal. The deforming may include, for example, melting, pressing, stamping, cutting, or other suitable steps that may be performed consecutively or simultaneously. The deforming may also be performed simultaneously with the sealing of the distal end of the delivery tube. In some embodiments, at least some of the deforming steps are performed prior to filling the reservoir 100 and sealing the dispenser 1. For example, the fingers 322 may be formed, and a pre-form of the removable seal 340 (e.g., the removable tab 342 and the breakable extension 346) may be formed prior to filling the reservoir 100. The passage 203 may extend through the pre-form of the removable seal 340 to facilitate filling. The pre-form may then be formed into the removable seal 340 (e.g., the removable tab 342 and the breakable extension 346) and the passage 203 be closed to seal the dispenser 1.

In a preferred embodiment the passage is sealed at a location upstream of the applicator element. The resulting dispenser 1, including the reservoir 100, the delivery tube 200, the applicator element 300, and the removable seal may be integrally formed from one continuous piece of plastic.

The delivery tube may be provided with a feature that helps the removable seal (e.g., the breakable extension) to break in a desired location. For example, the delivery tube may be provided with a groove or cut to guide the breaking of the removable seal (for example, cuts 347 discussed previously). The groove or cut may be positioned perpendicular with the longitudinal axis of the delivery tube, or may be disposed at a non-perpendicular angle.

In some embodiments, the reservoir and delivery tube are not sealed, but are closed by a separate closure formed in a separate molding step.

The method may further include creating a bend in the delivery tube. For example, the delivery tube can be shaped when the molded plastic is still warm and pliable.

The dispenser 100 may be provided with a label or printed, molded, or engraved lettering, numbering, or other insignia, to provide information about the contents, manufacturer, use, safety, expiration, etc.

In order to use the dispenser 100, a user may break or remove the removable seal to create an opening in the passage to allow liquid to flow into the applicator element. For example, the user may pinch the removable tab between his or her fingers and twist, turn, and/or bend the removable tab to break the breakable extension and to break the seal. For example, the user may rotate the removable tab about the longitudinal axis of the delivery tube to break off the tab and breakable extension. The liquid in the reservoir can then be applied by applying force to (e.g., squeezing) the reservoir and applying the liquid with the applicator element to a desired location. For example, the liquid can be applied to treat a patient or client in a dental care, oral care, health care, or personal care setting.

According to an embodiment, the opening 205 is upstream of the applicator element 300, 1300 or at least a portion of the applicator element 300, 1300 (e.g., upstream of the applicator tip 320, 1320 or a distal portion or distal end of the applicator tip 320, 1320). When the liquid is pushed out of the reservoir 100, the liquid 150 exits the delivery tube 200 through the opening 205 upstream of the applicator element 300, 1300 or at least a portion of the applicator element 300, 1300 and first flows onto the applicator tip 320, 1320 or a portion of the applicator tip 320, 1320. The liquid can then be applied to a surface using the applicator tip 320, 1320. In some embodiments the surface is the surface of a tooth, the gums, skin, or mucous membrane.

The complete disclosures of the patents, patent documents, and publications identified herein are incorporated by reference in their entirety as if each were individually incorporated. To the extent there is a conflict or discrepancy between this document and the disclosure in any such incorporated document, this document will control.

From the above disclosure of the general principles of the present invention and the preceding detailed description, those skilled in this art will readily comprehend the various modifications, re-arrangements and substitutions to which the present invention is susceptible, as well as the various advantages and benefits the present invention may provide. Therefore, the scope of the invention should be limited only by the following claims and equivalents thereof. In addition, it is understood to be within the scope of the present invention that the disclosed and claimed articles and methods may be useful in applications other than surgical procedures. Therefore, the scope of the invention may be broadened to include the use of the claimed and disclosed methods for such other applications.

What is claimed is:

1. A dispenser for liquids, the dispenser comprising:
    a reservoir defining a volume for housing a liquid;
    a delivery tube comprising a first end attached to the reservoir, and a second end distal from the reservoir, the delivery tube comprising a passage in fluid communication with the volume of the reservoir and extending away from the reservoir,
        wherein the delivery tube is at an angle of about 30° to 60° relative to the reservoir;
    an applicator element comprising an applicator tip and a base attached to the second end of the delivery tube, the applicator tip comprising a plurality of fingers extending away from the base to a distal end of the applicator element distal from the delivery tube; and
    a removable seal, wherein removal of the removable seal creates an opening in the passage at a location upstream of the applicator tip and a fluid distribution channel between the fingers.

2. The dispenser of claim 1, wherein the applicator element and the removable seal are integrally formed to the delivery tube.

3. The dispenser of claim 1, wherein the reservoir, the delivery tube, the applicator, and the removable seal are integrally formed.

4. The dispenser of claim 1, wherein the reservoir is made of a resilient material.

5. The dispenser of claim 1, wherein the reservoir comprises polyolefins, polyethylene, polypropylene, ethylene/propylene copolymer, polyester, polyamide, polyacrylate, polystyrene, or a combination thereof.

6. The dispenser of claim 1, wherein the reservoir is transparent or translucent.

7. The dispenser of claim 1, wherein the reservoir is opaque.

8. The dispenser of claim 1, wherein the delivery tube is tapered from a first cross-sectional area proximal to the reservoir to a second cross-sectional area distal to the reservoir.

9. The dispenser of claim 1, wherein the plurality of fingers is arranged in a plane.

10. The dispenser of claim 1, wherein the plurality of fingers is arranged circumferentially about the fluid distribution channel.

11. The dispenser of claim 1, wherein the removable seal comprises a removable tab disposed distally of the applicator.

12. The dispenser of claim 1, wherein the removable seal comprises a breakable extension extending between the passage of the delivery tube and the removable tab.

13. The dispenser of claim 1 further comprising a liquid within the volume of the reservoir.

14. The dispenser of claim 13, wherein the liquid comprises a viscosity from about 5 to about 300 Pas at a shear rate of 1.0/s, and wherein the opening has a size suitable for dispensing the liquid.

15. A method for making a dispenser of claim 1 for liquids, the method comprising:
    blow molding a reservoir defining a volume for housing a liquid and a delivery tube attached to the reservoir, the delivery tube comprising a proximal end adjacent the reservoir, a distal end extending away from the reservoir, and a passage in fluid communication with the volume of the reservoir, the passage extending from the proximal end to the distal end;
    adding liquid to the reservoir; and
    deforming the distal end of the passage to create an applicator.

16. The method of claim 15, further comprising sealing the distal end of the delivery tube.

17. The method of claim 15, wherein deforming the distal end comprises forming a removable seal, wherein removal of the removable seal creates an opening in the passage at a location upstream of the applicator.

18. The method of claim 15, further comprising closing the passage with a closure.

* * * * *